United States Patent

Hersperger et al.

[11] Patent Number: 5,925,649
[45] Date of Patent: Jul. 20, 1999

[54] ASCOMYCINS

[75] Inventors: René Hersperger, Münchenstein; Reto Naef, Rheinfelden, both of Switzerland

[73] Assignee: Novartis AG, Basel, Switzerland

[21] Appl. No.: 08/930,730

[22] PCT Filed: Apr. 4, 1996

[86] PCT No.: PCT/EP96/01492

§ 371 Date: Oct. 2, 1997

§ 102(e) Date: Oct. 2, 1997

[87] PCT Pub. No.: WO96/31514

PCT Pub. Date: Oct. 10, 1996

[30] Foreign Application Priority Data

| Apr. 6, 1995 | [GB] | United Kingdom | 9507128 |
| Dec. 20, 1995 | [GB] | United Kingdom | 9526049 |
| Dec. 20, 1995 | [GB] | United Kingdom | 9526050 |

[51] Int. Cl.⁶ .......................... A01N 43/42; C07D 267/22
[52] U.S. Cl. .......................... 514/291; 514/295; 540/456; 540/457
[58] Field of Search .................... 540/456, 457; 514/291, 295

[56] References Cited

U.S. PATENT DOCUMENTS

| 3,244,592 | 4/1966 | Arai | 167/65 |
| 4,929,611 | 5/1990 | Okuhara et al. | 514/183 |

FOREIGN PATENT DOCUMENTS

| 0315973 A2 | 5/1989 | European Pat. Off. . |
| 0323042 A1 | 7/1989 | European Pat. Off. . |
| 0423714 A2 | 4/1991 | European Pat. Off. . |
| 0427680 A1 | 5/1991 | European Pat. Off. . |
| 0465426 A1 | 1/1992 | European Pat. Off. . |
| 0474126 A1 | 3/1992 | European Pat. Off. . |
| 0484936 A1 | 5/1992 | European Pat. Off. . |
| 0532088 A1 | 3/1993 | European Pat. Off. . |
| 0532089 A1 | 3/1993 | European Pat. Off. . |
| 63-17884 | 1/1988 | Japan . |
| 91/02736 | 3/1991 | WIPO . |
| 91/13899 | 9/1991 | WIPO . |
| 91/19495 | 12/1991 | WIPO . |
| 93/05059 | 3/1993 | WIPO . |
| 94/21643 | 9/1994 | WIPO . |
| 96/13249 | 5/1996 | WIPO . |

OTHER PUBLICATIONS

Chemical Abstracts, vol. 109, No. 23, Abstract No. 210803, p. 640, 1988.
J. Funk, et al., J. Am. Acad. Dermatol., vol. 31, 1994, pp. 999–1014.
T. Fukuda, et al., Int. Arch. Allergy Appl. Immunol., vol. 94, 1991, pp. 259–261.

*Primary Examiner*—Richard L. Raymond
*Assistant Examiner*—Tamthom T. Ngo
*Attorney, Agent, or Firm*—Carol A. Loeschorn

[57] ABSTRACT

The invention provides novel ascomycins bearing one or more physiologically hydrolyzable and acceptable oxycarbonyl moieties or carboxy moieties, such compounds being found useful as pharmaceuticals, especially in the treatment of asthma an dermatitis. Methods of producing the compounds and pharmaceutical compositions comprising the compounds are also provided.

15 Claims, No Drawings

ASCOMYCINS

This is a 371 application of PCT/EP 96/01492, filed on Apr. 4, 1996.

This invention relates to novel ascomycins having pharmaceutical, e.g, antiinflammatory, activity. The invention also provides processes for making these novel compounds and pharmaceutical compositions comprising the same.

Ascomycins, of which FK-506 and Ascomycin itself are the best known, comprise a class of lactam macrolides, many of which have potent immunosuppressive or antiinflammatory activity. FK506 is a macrolide immunosuppressant produceable by *Streptomyces tsukubaensis* No 9993. The structure of FK506 is given in the appendix to the Merck Index, 11th ed. (1989) as item A5. Ascomycin is described, e.g., in U.S. Pat. No. 3,244,592. A large number of related compounds which retain the basic structure of FK506 and Ascomycin are also known. These compounds are described in various publications, for example EP 184162, EP 315973, EP 323042, EP 423714, EP 427680, EP 465426, EP 474126, WO 91/02736, WO 91/13899, WO 91/19495, EP 484936, EP 532088, EP 532089, WO 93/5059 and the like. Ascomycin, FK-506 and their structurally similar analogues and derivatives are termed collectively "ascomycins" in this specification.

As a class, ascomycins are potent immunosuppressive and anti-inflammatory compounds, but their pharmaceutical utility is limited by their toxicity. FK-506, for example, may be toxic to the kidneys, liver, and central nervous system at pharmaceutically relevant dosages. Additionally, while systemic immunosuppression may be desirable for some conditions, e.g., graft rejection, it is generally undesirable for the treatment of local inflammatory conditions, e.g., asthma or dermatitis.

It has now surprisingly been discovered that certain ascomycins bearing one or more physiologically hydrolyzable and acceptable oxycarbonyl moieties are highly effective locally active anti-inflammatory agents, e.g., on the skin and airways, but are "soft" drugs, that is they are rapidly transformed in vivo to ascomycins bearing unprotected carboxy groups, which compounds are not systemically active. It is further surprisingly discovered that the corresponding ascomycins bearing unprotected carboxy groups, although much less intrinsically active than the physiologically hydrolyzable oxycarbonyl moieties, nevertheless are highly potent topically, especially dermally. Both the acid and ester forms of the ascomycins described herein are well tolerated and, unlike currently available ascomycins, they do not produce systemic immunosuppression or significant systemic side effects at pharmacologically active dosages.

An ascomycin of the invention is thus an ascomycin bearing one or more physiologically hydrolyzable and acceptable oxycarbonyl moieties or one or more carboxy moieties, which is useful in the manufacture of a systemically nonimmunosuppressive, locally active medicament for topical application, e.g., to the skin or airways, e.g., a compound of formula I, Ia, or Ib, as described and exemplified below.

The physiologically hydrolyzable and acceptable oxycarbonyl or carboxy moiety or moieties are suitably linked to the ascomycin through a non-metabolically labile spacer of from 1 to 18 carbon units in length, preferably 6–8 carbon units, and optionally comprising a cyclic (e.g. aromatic) or branched structure and/or one or more heteroatoms, e.g., nitrogen, oxygen or sulfur. Preferably, the spacer comprises an arylene moiety, e.g., a phenylene moiety. In measuring the length of the spacer moiety, it is understood that the length is the length of longest consecutive chain of atoms in the moiety, not counting side chains or the bridge portion of cyclic structures. Thus, a p-phenylcarbamoyl spacer, for example, would be considered to have a length of 6 carbon units—four for the p-phenylene, one for the nitrogen and one for the carbonyl. This spacer is suitably attached to the ascomycin via the hydroxy at the 4-position on the cyclohexyl ring of the ascomycin (i.e., position 28, using the standard numbering for FK-506), e.g., by an O-carbamate or O-thiocarbamate coupling. For example, the invention includes a 28-O-carbamoyl- or 28-O-thiocarbamoyl-ascomycin, wherein the carbamoyl or thiocarbamoyl moiety is not metabolically labile but bears or is linked to one or more (e.g., up to 4) carboxy or physiologically hydrolyzable moieties, preferably via a carbon chain of up to 16, preferably 4–6 carbon units in length, preferably comprising a phenylene moiety. By "systemically nonimmunosuppressive, locally active" is meant a compound which is at least 10 more active on local administration than on intravenous administration in a suitable inflammatory model, for example at least 10× more active when given by the inhaled route than by the i.v. route in the sensitized Brown-Norway rat model described below.

By physiologically hydrolyzable and acceptable oxycarbonyl is meant a moiety of formula RO-CO-, which is cleavable under physiologic conditions to yield (i) an alcohol (ROH) which is tolerable at the dosages to be administered, and (ii) an ascomycin bearing one or more carboxy groups. Suitable oxycarbonyl moieties thus include e.g., alkoxycarbonyl, e.g., ($C_{1-6}$) alkoxycarbonyl, and aryloxycarbonyl; preferably methoxycarbonyl, ethoxycarbonyl, t-butoxycarbonyl, or benzyloxycarbonyl.

The ascomycins of the invention are preferably the compounds of Formula I:

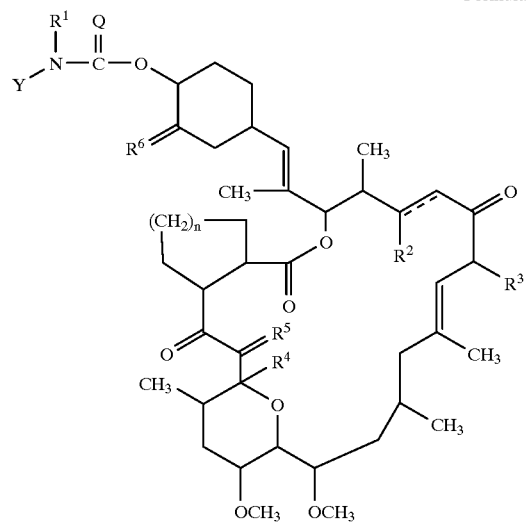

Formula I wherein

Y is a hydrocarbon form 1–16 carbon units in length (having a linear, branched, and/or cyclic (e.g. aromatic) structure and optionally comprising up to three heteroatoms, e.g. nitrogen, oxygen or sulfur) and bearing from 1 to 4 carboxy or physiologically hydrolyzable and acceptable oxycarbonyl moieties;

Z is selected from carboxy and physiologically hydrolyzable oxycarbonyl, or from an alkyl, alkoxy, alkylamino, or dialkyl-amino group bearing one to four carboxy or physiologically hydrolyzable oxycarbonyl moieties;

Q is O or S;

$R^1$ is H, alkyl, or aryl;

$R^2$ is hydrogen or hydroxy;

$R^3$ is methyl, ethyl, propyl or allyl;

$R^4$ is hydroxy or alkoxy;
$R^5$ is oxo or (H, OH);
$R^6$ is oxo, (H, OH), or (H, alkoxy);
n is 1 or 2; and
the bond depicted by parallel solid and dotted lines is either a single or double bond;
provided that when $R^1$ is alkyl or aryl, then Y is carboxymethyl or (physiologically hydrolyzable and acceptable oxycarbonyl)methyl or is aryl or (alkyl-, alkoxy-, alkylamino-, or dialkyl-amino)-aryl bearing from 1 to 4 carboxy or physiologically hydrolyzable and acceptable oxycarbonyl moieties;
in free or pharmaceutically acceptable salt form.

The substituents for formula I are, independently, preferably as follows:

Y is preferably (i) alkyl, aryl, alkaryl, alkoxyaryl, aralkyl, alk- or dialk-aminoalkyl, or alk- or dialk-aminoaryl bearing from 1 to 4 physiologically hydrolyzable and acceptable oxycarbonyl moieties, or (ii) alkyl, aryl, alkaryl, alkoxyaryl, aralkyl, alk- or dialk-aminoalkyl, or alk- or dialk-aminoaryl bearing from 1 to 4 carboxy moieties. Most preferably, Y is carboxymethyl or (physiologically hydrolyzable and acceptable oxycarbonyl)methyl or is aryl or (alkyl-, alkoxy-, alkylamino-, or dialkyl-amino)-aryl bearing from 1 to 4 carboxy or physiologically hydrolyzable and acceptable oxycarbonyl moieties.

Q is preferably O.
$R^1$ is preferably H, alkyl or benzyl, e.g., H, methyl, benzyl, most preferably H.
$R^2$ is preferably hydroxy.
$R^3$ is preferably ethyl or allyl.
$R^4$ is preferably hydroxy.
$R^5$ is preferably oxo.
$R^6$ is preferably (H, methoxy).
n is preferably 2.

The bond depicted by parallel solid and dotted lines is preferably a single bond.

Especially preferred compounds of formula I are the compounds of formula Ia:

Formula Ia

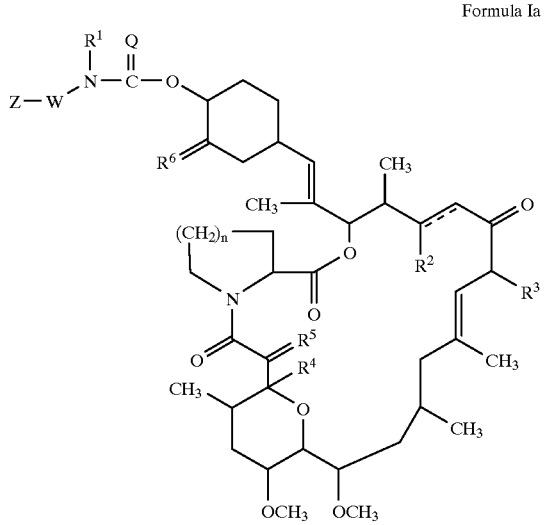

wherein Q, $R^1$ through $R^6$, n, and the dotted line are as defined above,
W is methylene or phenylene, and
Z is selected from carboxy and physiologically hydrolyzable and acceptable oxycarbonyl, and when W is phenylene, is also selected from alkyl, alkoxy, alkylamino, and dialkyl-amino group bearing one to four carboxy or physiologically hydrolyzable and acceptable oxycarbonyl moieties,
in free or pharmaceutically acceptable salt form.
Preferably, W is p-phenylene.

Where W is phenylene, e.g., p-phenylene, Z is preferably selected from benzyloxycarbonylalkyl, alkoxycarbonyl, (alkoxycarbonyl)$_{1-4}$alkyl, (alkoxycarbonylalkyl)$_{1-2}$amino, and alkoxycarbonylalkoxy, for example methoxycarbonylmethyl, ethoxycarbonylmethyl, benzyloxycarbonylmethyl, 2-(methoxycarbonyl)ethyl, 3-(methoxycarbonyl)propyl, methoxycarbonyl, 2-(methoxycarbonyl)ethenyl, methoxycarbonylmethoxy, di(methoxycarbonyl)-methyl, di(t-butoxycarbonyl)-methyl, 2-di(methoxycarbonyl)-ethyl, 1-(dimethoxycarbonyl-methyl)-2-di(methoxycarbonyl)-ethyl, or di(methoxycarbonylmethyl)amino, or from carboxy and carboxyalkyl, e.g., carboxymethyl. Where W is methylene, Z is preferably carboxy or alkoxycarbonyl, e.g., methoxycarbonyl or ethoxycarbonyl.

A particularly preferred class of compounds are thus the compounds of Formula Ib:

Formula Ib

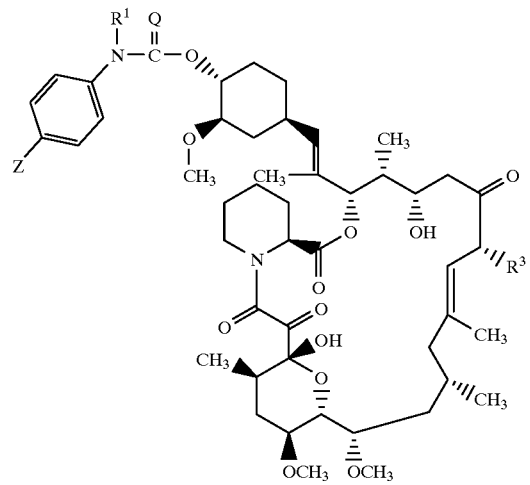

wherein Q, $R^1$, $R^3$, and Z are as defined above, in free or pharmaceutically acceptable salt form.

Most especially preferred are compounds of formula Ib wherein Q is O, $R^1$ is H, $R^3$ is ethyl or allyl, and Z is carboxymethyl or methoxycarbonylmethyl.

It is understood that the compounds of formula I, Ia, and Ib may exist in free form or may in some cases form salts, e.g., acid or base addition salts at the amino or carboxy groups respectively. All such pharmaceutically acceptable salt forms are considered to be comprised within the scope of this invention.

As used herein, the terms "alk-" or "alkyl" preferably refer to an aliphatic moiety of containing up to six carbon atoms (which may be branched, linear, or cyclic, optionally unsaturated, optionally interrupted by one or more ether (-O-) linkages and/or optionally substituted, e.g., with one or more halogen molecules), especially saturated branched or linear $C_{1-4}$alkyl; and "ar-" or "aryl" preferably refer to a single or double ring aromatic hydrocarbon group, e.g., phenyl, benzyl, tolyl, napthyl, or the like (which may be optionally substituted, e.g., with one or more halogen molecules), especially phenyl or benzyl.

It is understood that the compounds of Formula I, Ia or Ib may exist in the form of one or more isomers, stereoisomers, or tautomers, e.g., optical or geometric isomers due to the presence of asymmetric carbon atoms and double bonds, or tautomers due to enolization or other equilibrium rearrangements, which are also included within the scope of this invention. Preferably, the conformation is as for ascomycin or FK-506, e.g., as depicted in formula Ib.

Compounds of formula I, Ia and Ib are preferably made by reacting a 28-O-activated ascomycin (e.g., a compound of Formula I wherein the oxygen at the 4-position of the cyclohexyl ring bears an activating group rather than a carbomoyl or thiocarbamoyl moiety) with a compound of formula Y-N(R$^1$)H wherein Y and R$^1$ are as defined above (optionally in carboxy protected form, e.g., where Y bears one or more carboxy), deprotecting the product where required, and recovering the compound of formula I, Ia or Ib in free or salt form. The 28-O activated ascomycin is suitably prepared by reacting a parent ascomycin, e.g., a compound of formula I having hydroxy at the 4-position on the cyclohexyl ring, e.g., Ascomycin or FK-506, with an O-activating reagent, e.g. triphosgene for the carbamate compounds or thiophosgene for the thiocarbamate compounds, under suitable reaction conditions, e.g., preferably at low temperature (e.g., below 0° C., preferably below −60° C.) in the presence of an organic base. Optionally, the parent ascomycin may be hydroxy-protected to prevent activation other than at the desired location, and the reaction product deprotected either before or after introduction of the amino substituent, but this is not generally necessary, particularly if the activation is carried out at low temperatures, as the hydroxy group on the cyclohexyl ring of the ascomycin is generally significantly more accessible and reactive than the other hydroxy groups on the molecule.

Compounds of formula I, Ia and Ib also suitably prepared as follows:

(i) for preparation of a compound of formula I, Ia and Ib bearing one or more physiologically hydrolyzable and acceptable oxycarbonyl moieties, esterifying the corresponding ascomycin bearing one or more carboxy moieties with the corresponding alcohol, e.g., hydroxyalkyl, or hydroxyaryl for example methanol, ethanol, t-butanol, or benzyl alcohol; or (ii) for preparation of a compound of formula I, Ia and Ib bearing one or more carboxy moieties, hydrolysing the corresponding ascomycin bearing one or more oxycarbonyl moieties, and recovering the compound of formula I, Ia, or Ib in free or salt form.

The ascomycins of the invention have potent local immunosuppressive and anti-inflammatory activity. In particular they inhibit antigen-induced inflammatory cell infiltration, for example in the airways or skin. In vivo this activity is apparent following topical administration, e.g. following topical administration to the airways via the pulmonary route or administration to the skin. The ascomycins of the invention are in contrast found to possess substantially reduced, or to be substantially devoid of, activity, e.g. anti-inflammatory or immunosuppressive activity, in vivo when administered systemically, for example following oral or i.v. administration.

The immunosuppressive and anti-inflammatory properties of ascomycins of the invention may be demonstrated in standard test models in vitro and in vivo, e.g. as follows:

1. In vitro immunosuppression:

Murine mixed lymphocyte reaction

Ca. 0.5×10$^6$ lymphocytes from the spleen female (8–10 weeks) Balb/c mice are incubated for 5 days in 0.2 ml cell growth medium with ca. 0.5×10$^6$ lymphocytes from the spleen of female (8–10 weeks) CBA mice. Test substance is added to the medium at various concentrations. Activity is assessed by ability to suppress proliferation associated DNA synthesis as determined by incorporation of radiolabelled thymidine.

Ascomycins in accordance with the present invention having a physiologically hydrolyzable oxycarbonyl moiety inhibit thymidine incorporation at concentrations of the order of from 0.005 to 0.025 μg/ml. Compounds of examples 1, 2, 7, and 8 exhibit activity in this assay roughly equipotent to or only slightly less than FK-506 itself, with a relative IC$_{50}$ of from ca. 3 to ca. 15. The acid forms of these compounds, however, are significantly less active. For example, the compounds of examples 1 and 7 both convert in vivo to the acid of example 19, which has a relative IC$_{50}$ of about 150 in this assay.

2. Asthma model:

Allergen—induced pulmonary eosinophilia

Exposure of Brown Norway rats to inhaled antigen (ovalbumin, OA) evokes pulmonary eosinophilia that is maximal 48 hours later. In addition to eosinophil numbers, the activation status of these cells can be assessed by means of enzymatic activity of the eosinophil granule enzyme eosinophil peroxidase (EPO). In the present experiments, inhibition of pulmonary eosinophil accumulation by the ascomycins of the invention is assessed.

Ovalbumin (10 μg/ml) is mixed (1 hour on ice) in a blender with aluminum hydroxide (10 mg/ml) and injected s.c. coincidentally with a B. pertussis vaccine (0.25 ml/rat i.p.) into male Brown Norway rats (ca. 200 g). Injection of OA together with adjuvant is repeated 15 and 21 days later. On day 28, sensitized animals are restrained in plastic tubes and exposed for one hour to an aerosol of OA (3.2 mg/ml) using a nose only exposure system. Animals are killed 48 hours later with phenobarbital (250 mg/kg i.p.). The lungs are ravaged using 3 aliquots (4 ml) of Hank's solution (HBSS×10, 100 ml; EDTA 100 mM, 100 ml; HEPES 1M, 10 ml; 1 liter water), recovered cells are pooled, smeared air dried and stained to differentiate cell types. Cells are identified and counted under oil immersion (×1,000). A minimum of 500 cells per smear are counted and the total population of each cell type is calculated.

The relative efficacy via various routes of administration is assessed to determine whether activity is primarily local or systemic. For oral administration, test substance is administered p.o. suspended in tragacinth by gavage either 1 or 6 hours prior to and 24 hours after antigen exposure. For i.v. or i.p. administration, compound is dissolved in a mixture of ethanol (0.2%), PEG (66.7%) and water. For intratracheal administration, compound is adminstered as a powder suspended in saline containing DMSO (2.5%). For inhalation studies, test substance is micronised for delivery to test animals restrained within a flow-past, nose-only inhalation chamber. In all cases administration is effected 1 or 6 hours prior to and 24 hours after OA challenge.

In untreated animals OA challenge induces increase of all cell types in BAL fluid 24 hours after challenge. Prior administration of ascomycins in accordance with the present invention by inhalation at dosages of the order of from 0.1 to 15.0 mg/kg reduces eosinophil count in BAL in a dose dependent manner as compared with untreated controls. Cell counts for other leukocytes (macrophages, neutrophils) are also reduced. For example, compounds of examples 1, 2 and 7 below, following intratracheal administration at a dose of ca. 1 mg/kg or inhalation at a dose of ca. 0.4 mg/kg, are shown to inhibit eosinophil accumulation by more than 50%. In contrast with FK-506, which is very potent in this model whether given intravenously, intratracheally, saubcutaneously or by inhalation, the ascomycins of the invention, e.g., of examples 1, 2, and 7, are not measurably active or are at least 10× less active when given intravenously, orally, or subcutaneously, demonstrating that the activity is local rather than systemic.

3. Dermal models:

3.1: Allergic contact dermatitis in the mouse

Antiinflammatory activity of topically applied compounds is tested in a murine model of allergic contact dermatitis. Groups of 8 female NMRI mice (ca. 30 g) sensitized by epicutaneously applied 2% oxazolone are challenged with oxazolone on the right ear. After 30 minutes, the test sites are treated topically with 10 μl of the test compound (test groups) or with the vehicle alone (control groups). The left ears remain unchallenged and untreated. Activity is determined 24 hours after challenge by determination of pinnal weights as a measure of edema in test and control animals. Active compounds inhibit increase in pinnal weight.

The ascomycins of the invention, particularly those bearing one or more carboxy groups, show topical activity in this model on the same order as or somewhat higher than FK-506. The ascomycins of the invention having one or more carboxy moieties are especially potent topically. At concentrations of from 0.004–0.01%, the compound of example 20, for example, shows from 47% to 69% inhibition, compared to 57% inhibition for FK-506 at concentrations of 0.01%. Ascomycins of the invention having one or more physiologically hydrolyzable and acceptable oxycarbonyl moieties are also active, e.g., inhibiting pinnal swelling by approximately 35% at concentrations of 0.01% in the case of the compound of example 2.

3.2: Allergic contact dermatitis in domestic pigs

Antiinflammatory activity of topically applied compounds is tested in the swine model of allergic contact dermatitis, e.g., as described in J. Invest. Dermatol. (1992) 98: 851–855. Young domestic pigs sensitized with 2,4-dinitrofluorobenzene (DNFB) are challenged with 1% DNFB on 24 test sites on both dorsolateral sides of the back. The test sites are treated topically with the dissolved test compounds or the vehicle alone, 0.5 and 6 hours after challenge. One day after challenge gross changes of compound- and vehicle-treated sites were semiquantitatively evaluated. Active compounds inhibit erythema and infiltration.

The ascomycins of the invention show topical activity in this model on the same order as FK 506. Ascomycins of the invention bearing one or more carboxy moieties are somewhat more potent, so that at a concentration of 0.13%, for example, the compound of example 20 shows 49% inhibition compared to vehicle treated sites, and the compound of example 2 at the same concentration shows about 25% inhibition.

Ascomycins of the invention are accordingly useful for the treatment of diseases or conditions responsive to or requiring topical anti-inflammatory, immunosuppressive or related therapy, e.g. for topical administration for the treatment of such diseases or conditions of the eye, nasal passages, buccal cavity, or colon, and particularly of the skin or the airways or lung. In particular ascomycins of the invention permit topical anti-inflammatory, immunosuppressive or related therapy with the concomitant avoidance or reduction of undesirable systemic side-effects, for example general systemic immunosuppression.

Ascomycins of the invention are in particular useful for the treatment by inhalation of diseases and conditions of the airways or lung, in particular inflammatory or obstructive airways disease. They are especially useful for the treatment of diseases or conditions of the airways or lung associated with or characterized by inflammatory cell infiltration or other inflammatory event accompanied by inflammatory cell, e.g. eosinophil and/or neutrophil, accumulation. They are most especially useful for the treatment of asthma.

Ascomycins of the invention are useful in the treatment of asthma of whatever type or genesis including both intrinsic and, especially, extrinsic asthma. They are useful for the treatment of atopic or non-atopic asthma, exercise induced asthma, bronchitic asthma, including allergic asthma, bronchitic asthma exercise induced asthma, occupational asthma, asthma induced following bacterial infection and other non-allergic asthma. Treatment of asthma is also to be understood as embracing treatment of "wheezy-infant syndrome", that is treatment of subjects, e.g. of less that 4 or 5 years of age, exhibiting wheezing symptoms, in particular at night, and diagnosed or diagnosable as "wheezy infants", an established patient category of major medical concern and now more correctly identified as incipient or early-phase asthmatics. Ascomycins of the invention are in particular useful for the treatment of asthma in subjects whose asthmatic status is either steroid dependent or steroid resistant.

Ascomycins of the invention are also useful for the treatment of bronchitis or for the treatment of chronic or acute airways obstruction associated therewith. Ascomycins of the invention may be used for the treatment of bronchitis of whatever type or genesis, including, for example, acute bronchitis, arachidic bronchitis, catarrhal bronchitis, chronic bronchitis, croupous bronchitis, phthinoid bronchitis and so forth.

Ascomycins of the invention are in addition useful for the treatment of pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, berylliosis, chalicosis, ptilosis, siderosis, silicosis, tabacosis and, in particular, byssinosis.

Ascomycins of the invention may also be used for the treatment of eosinophil-related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Löffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug reaction.

The word "treatment" as used above in relation to the treatment of diseases of the airways and lungs, in particular asthma, is to be understood as embracing both symptomatic and prophylactic modes, that is the immediate treatment, e.g. of acute inflammation (symptomatic treatment) as well as advance treatment to prevent ameliorate or restrict long term symptomology (prophylactic treatment). The term "treatment" as used in the present specification and claims in relation to such diseases is to be interpreted accordingly as including both symptomatic and prophylactic treatment, e.g. in the case of asthma, symptomatic treatment to ameliorate acute inflammatory event and prophylactic treatment to restrict on-going inflammatory status and to ameliorate future bronchial exacerbation associated therewith.

Ascomycins of the invention may also be used to treat any disease or condition of the airways or lung requiring immunosuppressive therapy, e.g. for the treatment of autoimmune diseases of, or as they affect, the lungs (for example, for the treatment of sarcoidosis, alveolitis or chronic hypersensitivity pneumonitis) or for the maintenance of allogenic lung transplant, e.g. following lung or heart transplantation.

As previously indicated, for the above purposes, ascomycins of the invention will be administered topically within the airways, e.g. by the pulmonary route/by inhalation. As also previously noted, while having potent efficacy when administered topically, ascomycins of the invention are devoid of, or exhibit relatively reduced, systemic activity, e.g. following oral administration. Ascomycins of the invention thus provide a means for the treatment of diseases and conditions of the airways or lung, e.g. as hereinabove set forth, with the avoidance of unwanted systemic side effect, e.g. consequent to inadvertent swallowing of drug substance during inhalation therapy. (It is. estimated that during the course of manoeuvres required to effect administration by inhalation, up to 90% or more of total drug substance administered will normally be swallowed rather than inhaled).

By the provision of ascomycins which are topically active, e.g. effective when inhaled, but systemically inactive, the present invention makes ascomycin therapy available to subjects for whom such therapy might otherwise be excluded, e.g. due to the risk of systemic, in particular immunosuppressive, side effects.

The ascomycins of the invention (particularly those bearing a carboxy moiety) are also administered dermally, i.e. topically to the skin, for example for the treatment of cutaneous diseases mediated by immune mechanisms, e.g., psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, and other inflammatory or allergic conditions of the skin. Optionally, the ascomycins of the invention are co-administered together with anti-inflammatory, immunosuppressive, or other pharmacologically active agents, e.g., corticosteroids, antihistamines, antibiotics, antifungals, etc.

Ascomycins of the invention are also useful for the treatment of other diseases or conditions, in particular diseases or conditions having an autoimmune or inflammatory component and for which topical therapy my be practiced, for example, treatment of diseases and conditions of the eye such as conjunctivitis, keratoconjunctivitis sicca, and vernal conjunctivitis and maintenance of corneal transplant, diseases affecting the nose including allergic rhinitis, as well as diseases of the colon, for example Crohn's disease and ulcerative collitis.

For the above purposes, ascomycins of the invention may be employed in any dosage form appropriate for topical administration to the desired site.

Thus for the treatment of diseases of the airways or lungs ascomycins of the invention may be administered via the pulmonary route/by inhalation from an appropriate dispenser device. For this purpose ascomycins of the invention may be employed in any suitable finely dispersed or finely dispersible for, capable of administration into the airways or lungs, for example in finely divided dry particulate form or in dispersion or solution in any appropriate (i.e. pulmonarily administrable) solid or liquid carrier medium. For administration in dry particulate form, ascomycins of the invention may, for example, be employed as such, i.e. in micronised form without any additive materials, in dilution with other appropriate finely divided inert solid carrier or diluent (e.g. glucose, lactose, mannitol, sorbitol, ribose, mannose or xylose), in coated particulate form or in any other appropriate form as known in the art for the pulmonary administration of finely divided solids.

Pulmonary administration may be effected using any appropriate system as known in the art for delivering drug substance in dry or liquid form by inhalation, e.g. an atomizer, nebulizer, dry-powder inhaler or like device. Preferably a metered delivery device, i.e. capable of delivering a predetermined amount of ascomycin at each actuation, will be employed. Such devices are known in the art.

Suitable topical forms for the treatment of diseases or conditions of the skin will include, for example, creams, gels, ointments, pastes, cataplasms, plasters, transdermal patches and the like. Formulations for dermal application will appropriately contain a skin penetration enhancer, e.g. as known in the art, for example azone.

For nasal administration, ascomycins of the invention will suitably be administered in liquid form from a nasal applicator. Forms suitable for ophthalmic use will include lotions, tinctures, gels, ointments and ophthalmic inserts, again as known in the art. For rectal administration. i.e. for topical therapy of the colon, ascomycins of the invention may be administered in suppository or enema form, in particular in solution, e.g. in vegetable oil or like oily system for use as a retention enema.

The present invention accordingly further provides:

A. A method of treating a disease or condition requiring anti-inflammatory, immunosuppressive or related therapy in a subject in need thereof, which method comprises topically administering an effective amount of an ascomycin of the invention; as well as B. An ascomycin of the invention for use as a pharmaceutical, for example for use in treating a disease or condition requiring anti-inflammatory, immunosuppressive or related therapy, e.g. for use in a method as defined under A above.

The method as defined under A above applies in particular to the treatment of diseases and conditions of the eye, nose, throat, buccal cavity, or colon or, especially the airways, lungs or skin. It is applicable to any disease or condition as hereinbefore set forth. The ascomycins of the invention bearing a physiologically hydrolyzable and acceptable oxycarbonyl moiety or moieties are particularly well suited for treatment of diseases or conditions of the airways or lungs requiring anti-inflammatory or related therapy, including rejection of lung transplant, and especially any disease or condition of the airways or lungs characterized by inflammatory cell infiltration, e.g. for the treatment of asthma. The ascomycins of the invention bearing a carboxy moiety or moieties are especially well suited for treatment of diseases or conditions of the skin requiring anti-inflammatory or related therapy, e.g., for the treatment of psoriasis, contact dermatitis, atopic dermatitis, and other inflammatory or allergic conditions of the skin.

The present invention further provides:

C. A pharmaceutical composition for topical administration, i.e. in topically administrable form, comprising an ascomycin of the invention together with pharmaceutically acceptable diluent or carrier, or an ascomycin of the invention in a form or in a means or device enabling or facilitating topical administration.

Pharmaceutically acceptable diluents or carriers under C above are diluents or carriers acceptable for topical application at the intended side of therapy, e.g. diluents or carriers acceptable for topical administration pulmonarily, dermally, nasally, ocularly or rectally. Forms in topically administrable form, e.g. enabling or facilitating topical administration, include, e.g. dry powder preparations of the active ingredient (i.e. of the invention) in substantially pure form, for example as employed in the art for delivery from dry powder inhalation device. Means or devices enabling or facilitating topical administration include, in particular, inhalation devices as well as containers and the like from which the active ingredients may be delivered in a form capable of topical application. Preferred embodiments as defined under C will be (i) such as permit topical administration within the airways or lungs, e.g. by inhalation, in the case of ascomycins of the invention bearing one or more oxycarbonyl moieties, and (ii) such as to permit dermal administration, e.g., in the form of an ointment or cream, in the case of ascomycins of the invention bearing one or more carboxy moieties.

Dosages of ascomycins of the invention employed in practicing the method of the present invention will of course vary depending on the site of treatment, the particular condition to be treated, the severity of the condition, the subject to be treated (e.g. in terms of body weight, age and so forth) as well as the effect desired.

In general, for treating diseases or conditions of the airways or lungs, e.g. for use in treating inflammatory or obstructive airway disease, for example asthma, ascomycins of the invention will suitably be administered topically to the airways or lungs, e.g. by inhalation, at dosages of the order of from 0.01 to 50 mg/day, e.g. from 0.1–5 mg/day, most preferably from 0.4–1.6 mg/day, e.g. administered from a metered delivery system in a series of from 1 to 5 puffs at each administration, with administration performed once to four times daily, e.g., 200–800 µg once or twice a day by inhalation. Dosages at each administration will thus conveniently be of the order of from about 0.0025 to 10 mg, more suitably from 0.1 to 1.0 mg, e.g. administered with a metered delivery device, e.g. capable of delivering, e.g. 0.02 to 1.0 mg ascomycins, per actuation.

For the treatment of diseases of the eye and nose, ascomycins of the invention will generally be administered in the form of an appropriate composition, e.g. eye drop, gel, collyrium or the like or nasal drop, nasal spray or the like, comprising from about 0.005 to about 5%, especially from about 0.01 to about 1%, ascomycin by weight, in an ocularly or nasally applicable diluent or carrier for application to the surface of the eye or nasally in an amount of form about 0.05 to about 0.2 ml compositions, e.g. from about 0.05 to about 0.1 ml composition, once or from two to three times daily.

For the treatment of diseases or conditions of the colon, in general suitable daily dosages of ascomycins of the invention will be of the order of from about 0.01 to about 5, preferably from about 0.1 to about 1.0 mg/kg, suitably administered as a retention enema administered once or in divided doses 2× daily. Each administered dosage will thus suitably comprise from about 0.1 to about 350, preferably from about 1 to about 150, more preferably from about 5 to about 70 mg ascomycin of the invention together with an appropriate rectally applicable diluent or carrier therefor. Suitable ascomycin concentrations for use in such retention enema systems are of the order of from about 0.05 to about 2, preferably from about 0.1 to about 1.0 mg/ml.

For dermal administration for the treatment of diseases or conditions of the skin, ascomycins of the invention will generally be administered in appropriate, i.e. dermally applicable, form comprising a therapeutically effective concentration of the ascomycin of the invention, e.g. from ca. 0.001 to 10%, e.g. 0.004%–1% by weight of ascomycin of the invention, together with a dermally acceptable diluent or carrier therefor. Formulations for dermal administration may take the form of creams, ointments, gels, or transdermal delivery systems, e.g. patches and, in addition to inert diluents or carriers, may suitably contain skin penetration enhancing agents, analogously to formulations as known in the art. Such compositions will suitably be applied to the site of treatment in an amount of from ca. 0.005 to ca. 0.05 g/cm$^2$, 1, 2, or 3× daily.

EXAMPLES

Table 1 exemplifies compounds of formula Ib, wherein Z, Q, $R^1$ and $R^3$ are as specified. Bz signifies benzyl.

TABLE I

| Ex. | Z | $R^1$ | Q | $R^3$ | mp(° C.) |
|---|---|---|---|---|---|
| 1 | (CH$_3$O—CO)$_2$CH— | H | O | CH$_3$CH$_2$— | 115–120 |
| 2 | CH$_3$O—COCH$_2$— | H | O | CH$_2$=CHCH$_2$— | 105–109 |
| 3 | ((CH$_3$)$_3$CO—CO)$_2$CH— | H | O | CH$_3$CH$_2$— | 121–129 |
| 4 | (CH$_3$O—CO)$_2$CHCH$_2$— | H | O | CH$_3$CH$_2$— | 105–114 |
| 5 | ((CH$_3$O—CO)$_2$CH)$_2$CH— | H | O | CH$_3$CH$_2$— | 109–116 |
| 6 | (CH$_3$O—COCH$_2$)$_2$N— | H | O | CH$_3$CH$_2$— | 113–121 |
| 7 | CH$_3$O—COCH$_2$— | H | O | CH$_3$CH$_2$— | 115–120 |
| 8 | (CH$_3$O—CO)$_2$CH— | H | O | CH$_2$=CHCH$_2$— | 115–120 |
| 9 | CH$_3$CH$_2$O—COCH$_2$— | H | O | CH$_3$CH$_2$— | 110–116 |
| 10 | Bz—O—COCH$_2$— | H | O | CH$_3$CH$_2$— | 100–108 |
| 11 | CH$_3$O—COCH$_2$CH$_2$— | H | O | CH$_3$CH$_2$— | 104–111 |
| 12 | CH$_3$O—CO(CH$_2$)$_3$— | H | O | CH$_3$CH$_2$— | 105–109 |
| 13 | CH$_3$O—CO— | H | O | CH$_3$CH$_2$— | 115–121 |
| 14 | CH$_3$O—COCH=CH— | H | O | CH$_3$CH$_2$— | 115–123 |
| 15 | CH$_3$O—COCH$_2$O— | H | O | CH$_3$CH$_2$— | 110–115 |
| 16 | CH$_2$O—COCH$_2$— | CH$_3$— | O | CH$_3$CH$_2$— | 100–105 |
| 17 | CH$_3$O—CO— | H | S | CH$_3$CH$_2$— | 116–123 |
| 18 | (CH$_3$O—CO)$_2$CH— | H | S | CH$_3$CH$_2$— | 112–120 |
| 19 | HOOC—CH$_2$— | H | O | CH$_3$CH$_2$— | 132–135 |
| 20 | HOOC—CH$_2$— | H | O | CH$_2$=CHCH$_2$— | 135–138 |

Table II provides additional examples of compounds of formula I wherein $R^2$ and $R^4$ are hydroxy, $R^5$ is oxo, $R^6$ is (H, methoxy), n is 2, and the bond represented by parallel dotted and straight lines is a single bond, and Y, Q, $R^1$ and $R^3$ are as specified. The stereochemistry of all of the compounds is as for Formula Ib.

| Ex. | Y | Q | R¹ | R³ | mp °C. |
|---|---|---|---|---|---|
| 21 | CH₃CH₂O—CO—CH₂— | O | Bz | CH₃CH₂— | 94–100 |
| 22 | CH₃CH₂O—CO—CH₂— | O | H | CH₃CH₂— | 86–96 |
| 23 | CH₃CH₂O—CO—CH₂-p-C₆H₄—CH₂— | O | H | CH₃CH₂— | 92–99 |
| 24 | CH₃O—COCH₂CH₂(CH₃O—CO)CH— | O | H | CH₃CH₂— | 85–90 |
| 25 | C₆H₅—CH₂—(CH₃O—CO)CH— | S | H | CH₃CH₂— | 78–86 |
| 26 | CH₃O—COCH₂CH₂(CH₃O—CO)CH— | S | H | CH₃CH₂— | 93–105 |

Example 1 is prepared as follows:

To a solution of Ascomycin (6.0 g, 7.57 mmol) and 4-dimethylamino pyridine (4.62 g, 37.8 mmol) in 75 ml dichloromethane is added dropwise as solution of triphosgene (0.84 g, 2.83 mmol) in dichloromethane (15 ml) at −77 degrees Celsius. After 1 hour solid 2-(4-amino-phenyl)-malonic acid dimethyl ester (2.7 g, 12.1 mmol is added. The cooling bath is removed, and the suspension is allowed to warm to ambient temperature. The reaction mixture is stirred for another hour, and ethyl acetate and a saturated aqueous solution of NaCl are added. The organic phase is then washed twice (1N HCl) and evaporated to dryness to give a foamy residue which upon purification by flash chromatography yields pure product, mp 115°–120° C. (ethanol-water), (M+Li)⁺=1047.

Example 2 is prepared as follows:

To a solution of FK506 (10.0 g, 12.4 mmol) and 4-dimethylamino pyridine (7.5 g, 61.7 mmol) in 60 ml dichloromethane is added dropwise a solution of triphosgene (1.36 g, 4.6 mmol) in dichloromethane (40 ml) at −77° C. After one hour, methyl 4-amino-phenylacetic acid ester (3.1 g, 18.5 mmol) is added. The cooling bath is removed, and the suspension is allowed to warm to ambient temperature. The reaction mixture is stirred for another hour, and ethyl acetate and a saturated aqueous solution of NaCl are added. The organic phase is then washed twice (1N HCl) and evaporated to dryness to give a foamy residue which upon purification by flash chromatography yields pure product, mp 105–109° C. (ethanol-water); (M+Li)⁺=1001; ¹³C-NMR (CDCl₃), selected data: 212.79, 298.10, 172.03, 153.04, 137.03, 129.76, 119.75, 96.90, 51.94, 40.41, 39.57, 9.30.

Examples 3–18 and 21–26 are made analogously, using Ascomycin as starting material when R³ is ethyl and FK506 as starting material when R³ is allyl, and substituting the corresponding molar amounts of amines of formula X-Y-N(R¹)H (wherein X, Y and R¹ are as defined above) for the 2-(4-amino-phenyl)-malonic acid dimethyl ester of example 1 or the 4-aminophenylacetic acid methyl ester of example 2. Thiocarbamide compounds (i.e., where Q is S) are made analogously using thiophosgene in place of triphosgene as the activating reagent.

Example 19 is prepared as follows:

To a solution of Ascomycin (6.0 g, 7.57 mmol) and 4-dimethylamino pyridine (4.62 g, 37.8 mmol) in 75 ml dichloromethane is added dropwise as solution of triphosgene (0.84 g, 2.83 mmol) in dichloromethane (15 ml) at −77° C. After 1 hour, trimethylsilyl 4-amino-phenylacetic acid ester (12.1 mmol)) is added. The cooling bath is removed, and the suspension is allowed to warm to ambient temperature. The reaction mixture is stirred for another hour, and ethyl acetate and a saturated aqueous solution of NaCl are added. The organic phase is then washed twice (1N HCl) and evaporated to dryness to give a residue which is purified by flash chromatography. The resulting product is optionally further purified by precipitation from ethanol-water. The pure compound has a melting point of 132–135° C.

Example 20 is prepared as for example 19 using FK-506 as starting material in lieu of ascomycin, to produce the pure compound having a melting point of 135–138° C.

We claim:

1. A compound of Formula Ia:

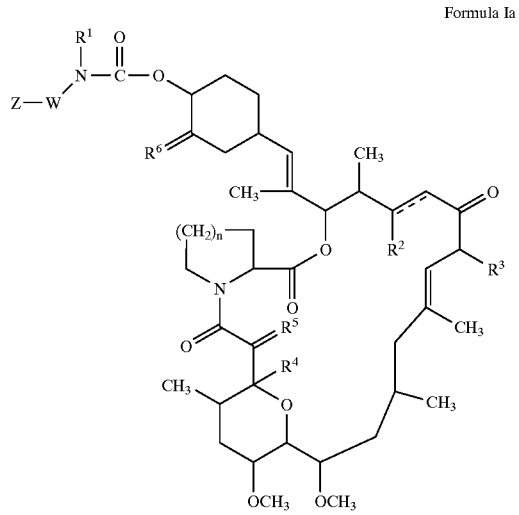

Formula Ia wherein

W is phenylene;

Z is selected from carboxy, physiologically hydrolyzable and acceptable oxycarbonyl, or from an alkyl, alkoxy, alkylamino, or dialkylamino group, said alkyl, alkoxy, alkylamino or dialkylamino group bearing one to four carboxy or physiologically hydrolyzable and acceptable oxycarbonyl moieties;

Q is O or S;

R¹ is H, alkyl, or aryl;

R² is hydrogen or hydroxy;

R³ is methyl, ethyl, propyl or allyl;

R⁴ is hydroxy or alkoxy;

R⁵ is oxo or (H, OH);

R⁵ is oxo, (H, OH), or (H, alkoxy);

n is an integer 1 or 2; and the bond depicted by parallel solid and dotted lines is either a single or double bond;

in free or physiologically acceptable salt form.

2. A compound according to claim 1 of Formula Ib:

Formula Ib

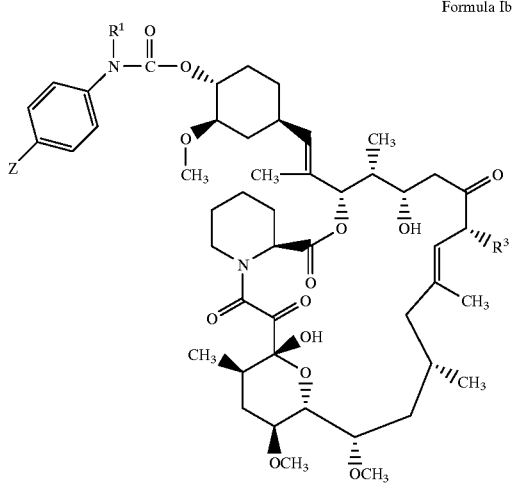

wherein Q, $R^1$, $R^3$ and Z are as defined in claim 1 for formula Ia, in free or pharmaceutically acceptable salt form.

3. A compound according to claim 2 of formula Ib wherein Q is O, $R^1$ is H, $R^3$ is ethyl or allyl, and Z is carboxymethyl or methoxycarbonylmethyl.

4. A compound according to claim 1 wherein Z is carboxy or is an alkyl, alkoxy, alkylamino, or dialkylamino group, said alkyl, alkoxy, alkylamino or dialkylamino group bearing one to four carboxy moieties.

5. A compound according to claim 1 wherein Z is physiologically hydrolyzable and acceptable oxycarbonyl or is an alkyl, alkoxy, alkylamino, or dialkylamino group, said alkyl, alkoxy, alkylamino or dialkylamino group bearing one to four physiologically hydrolyzable and acceptable oxycarbonyl moieties.

6. A compound according to claim 3 wherein $R^3$ is allyl, and Z is methoxycarbonylmethyl.

7. A compound according to claim 3 wherein $R^3$ is allyl, and Z is carboxymethyl.

8. Pharmaceutical compositions comprising a compound according to claim 1, optionally in combination or association with a pharmaceutically acceptable diluent or carrier.

9. A pharmaceutical composition according to claim 8 comprising a compound according to claim 4 for the treatment of an inflammatory or autoimmune disease of the skin by topical application.

10. A pharmaceutical composition according to claim 8 comprising a compound according to claim 5 for the treatment of asthma by inhalation.

11. A method for the treatment of an inflammatory or autoimmune disease of the skin, comprising administering a therapeutically effective amount of a compound according to claim 4 to a subject in need of such treatment.

12. A method for the treatment of an inflammatory or autoimmune disease of the skin, comprising administering a therapeutically effective amount of a compound according to claim 7 to a subject in need of such treatment.

13. A method for the treatment of asthma, comprising administering a therapeutically effective amount of a compound according to claim 5 to a subject in need of such treatment.

14. A method for the treatment of asthma, comprising administering a therapeutically effective amount of a compound according to claim 6 to a subject in need of such treatment.

15. A process for the production of a compound according to claim 1 comprising the steps of (i) reacting a 28-O-activated ascomycin with a compound of formula Z-Y-N($R^1$)H wherein Z, Y and $R^1$ are as defined in claim 1 and deprotecting, if required; or (ii) for preparation of a compound wherein Z comprises a physiologically hydrolyzable and acceptable oxycarbonyl moiety, esterifying the corresponding ascomycin wherein Z comprises carboxy with the corresponding alcohol; or (iii) for preparation of a compound wherein Z comprises carboxy, hydrolyzing the corresponding ascomycin wherein Z comprises an oxycarbonyl moiety;

and recovering the compound of formula Ia in free or salt form.

* * * * *